(12) United States Patent
Beaty

(10) Patent No.: US 10,481,083 B2
(45) Date of Patent: Nov. 19, 2019

(54) DETERMINATION OF BLOOD VOLUME IN A CULTURE BOTTLE

(75) Inventor: Patrick Shawn Beaty, Dallastown, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1281 days.

(21) Appl. No.: 12/867,980

(22) PCT Filed: Feb. 19, 2008

(86) PCT No.: PCT/US2008/002174
§ 371 (c)(1),
(2), (4) Date: Oct. 19, 2010

(87) PCT Pub. No.: WO2009/105062
PCT Pub. Date: Aug. 27, 2009

(65) Prior Publication Data
US 2011/0029249 A1    Feb. 3, 2011

(51) Int. Cl.
G01N 21/27    (2006.01)
G01N 21/64    (2006.01)
G16H 40/63    (2018.01)
G06F 19/00    (2018.01)
G01N 21/31    (2006.01)

(52) U.S. Cl.
CPC ......... *G01N 21/27* (2013.01); *G01N 21/6428* (2013.01); *G06F 19/00* (2013.01); *G16H 40/63* (2018.01); *G01N 2021/3144* (2013.01); *Y02A 90/26* (2018.01)

(58) Field of Classification Search
CPC ..................................................... G01N 21/27
USPC .......................................................... 702/19
See application file for complete search history.

(56) References Cited

U.S. PATENT DOCUMENTS

| | | | |
|---|---|---|---|
| 4,298,011 A | 11/1981 | Mangurten et al. | |
| 4,889,992 A | 12/1989 | Hoberman | |
| 5,770,394 A | 6/1998 | Berndt | |
| 6,096,272 A | 8/2000 | Clark et al. | |
| 6,395,506 B1 | 5/2002 | Pitner et al. | |
| 6,432,697 B1 | 8/2002 | Tice et al. | |
| 6,617,127 B2 | 9/2003 | Quaedflieg et al. | |
| 6,900,030 B2 | 5/2005 | Pitner et al. | |
| 2003/0009399 A1 | 1/2003 | Boerner | |
| 2005/0003712 A1 | 1/2005 | Sasaki et al. | |
| 2005/0037512 A1 | 2/2005 | Yeh et al. | |

FOREIGN PATENT DOCUMENTS

| | | |
|---|---|---|
| EP | 0645617 | 3/1995 |
| EP | 1014697 A2 | 6/2000 |
| WO | 2006023470 A1 | 3/2006 |
| WO | 2006071800 A1 | 7/2006 |

OTHER PUBLICATIONS

International Search Report for Application No. PCT/US08/02174 dated Jul. 18, 2008.
Oberoi et al., 2004, "Comparison of rapid colorimetric method with conventional method in the isolation of mycobacterium tuberculosis," Indian J Med Microbiol 22:44-46.
Stanier et al., 1986, The Microbial World, 5th edition, Prentice-Hall, Englewood Cliffs, New Jersey, pp. 10-20,33-37, and 190-195.
European Search Report for Application No. EP08725772 dated Oct. 30, 2014.
"Automated Blood Culture, BACTEC™ 9240/9120/9050", 9000 bc2, revision B, (Jul. 25, 2001), pp. 1-21, retrieved from internet at http://legacy.bd.com/ds/technicalCenter/clsi/clsi-9000bc2.pdf.
European Search Report dated Jan. 31, 2018 received in application No. 08725772.1; pp. 9.

*Primary Examiner* — Jerry Lin
(74) *Attorney, Agent, or Firm* — Botos Churchill IP Law LLP

(57) ABSTRACT

Systems, methods and apparatus for determining an amount of blood in a blood culture are provided where an initial biological state and then periodic measurements of the biological state of the culture are taken. For each respective measurement, a normalization relative value between the respective measurement and the initial measurement is made thereby forming normalization relative values. For each interval of time points represented by the normalization relative values, a first derivative of the normalization relative values in the interval is made thereby forming a plurality of rate transformation values. For each set of rate transformation values in the plurality of rate transformation values, an average relative transformation value is computed, thereby forming average relative transformation values. A lookup table that matches a measure of central tendency of the average relative transformation values to a blood amount is used to determine the amount of blood in the culture.

22 Claims, 9 Drawing Sheets

DETERMINATION OF BLOOD VOLUME IN A CULTURE BOTTLE

CROSS-REFERENCE TO RELATED APPLICATIONS

The present application is a national phase entry under 35 U.S.C. § 371 of International Application No. PCT/US2008/002174, which was filed on Feb. 19, 2008 and published in English as International Publication No. WO 2009/105062 A1.

1 FIELD OF THE INVENTION

Disclosed are improved systems and methods for determining the amount of blood in a blood culture in a vessel.

2 BACKGROUND OF THE INVENTION

Rapid and reliable detection of microorganisms in the blood is among the most important functions of the clinical microbiology laboratory. Several different blood culture systems and approaches are available to laboratories. For example the BACTEC® radiometric and nonradiometric systems (Becton Dickenson Diagnostic Instrument Systems, Sparks, Md.) are often used for this task. For example, the BACTEC® 9240 instrument accommodates up to 240 blood culture vessels and serves as an incubator, agitator, and detection system. Each vessel contains a fluorescent $CO_2$ sensor, and the sensors are monitored on a continuous basis (e.g., every ten minutes). Cultures are recognized as positive by computer algorithms for growth detection based on an increasing rate of change as well as sustained increase in $CO_2$ production rather than by the use of growth index threshold or delta values. The BACTEC® 9240 is completely automated once the vessels have been loaded.

Optimal performance of a blood culture system, such as the BACTEC® 9240, is dependent on collecting the correct amount of blood per sample. Culture of a sample below the optimal level can affect organism recovery based on a decreased probability of obtaining viable organisms from the limited blood volume. Culture of a sample above the optimum level can reduce the recovery of viable organisms by failing to properly dilute or remove inhibitors in the sample or by creating an unfavorable competitive situation with blood competing with any microbes present in the specimen for nutrients such as oxygen or sugar and thereby exceeding the design properties of the culture medium. Blood can also affect the performance of the system by masking the presence of growth when it is present. For example, it is possible for the acceleration of signal used to detect the presence of microorganisms to be homogenized into the blood background signal when too much or too little blood is cultured.

Given the above-background, what are needed in the art are methods for determining the amount of blood in a culture. The ability to determine the amount of blood in a culture in practice would, for example, allow a feedback system on the quality of the blood cultures (including phlebotomy feedback), the ability to identify vessels that are extremely over or under filled during protocol (to warn the staff that quality of the culture is compromised) and to adjust internal growth detection algorithms based on the presence of different levels of blood.

3 SUMMARY OF THE INVENTION

To meet the needs identified in the prior art, systems, methods and apparatus for determining an amount of blood (e.g., a volume of blood) in a blood culture vessel are provided. Data transformation methods have been devised, for example, that provide an estimate of the rate of metabolism and the change in rate of metabolism with time that allows an estimate of the initial rates of metabolic activity in the blood culture vessel that can be standardized to the amount of blood present and allow an estimate of the amount of blood in the blood culture. This blood volume determination may be used for immediate feedback to the user in the case where too much blood is added to a vial. This could result in prompting the user to split the specimen for more accurate results. As such, the systems and methods of the present invention can provide a number of applications useful in microbiology and related fields, and finds particular application in cell culture sterility test procedures.

In one aspect, the present invention provides a method of determining an amount of blood in a blood culture in a vessel. In the method, an initial biological state of the blood culture in the vessel is measured at an initial time point. Then, a plurality of measurements of a biological state of the blood culture in the vessel is taken, where each measurement in the plurality of measurements is at a different time point between a first time point and a second time point. For each respective measurement in the plurality of measurements, a normalization relative value is calculated between the respective measurement and the initial biological state of the blood culture thereby forming a plurality of normalization relative values. The plurality of normalization relative values can be broken down, on a timewise basis, into predetermined fixed intervals of time points between the first time point and the second time point. For instance, a first predetermined fixed interval may include the first ten normalization relative values, a second predetermined fixed interval may include the next ten normalization relative values and so forth until the second time point is reached. For each of these respective predetermined fixed intervals of time points between the first time point and the second time point, a first derivative of the normalization relative values in the respective predetermined fixed interval is determined, thereby forming a plurality of rate transformation values.

In such an embodiment, there is a rate transformation value for each predetermined fixed interval of time points. The plurality of rate transformation values can be considered as comprising a plurality of sets of rate transformation values. Each respective set of rate transformation values is for a different set of contiguous time points between the first time point and the second time point. For example, the first set of rate transformation values may be the first seven rate transformation values in the plurality of rate transformation values, the second set of rate transformation values may be the next seven rate transformation values in the plurality of rate transformation values, and so forth. For each respective set of rate transformation values in the plurality of sets of rate transformation values, an average relative transformation value is computed as a measure of central tendency of each of the rate transformation values in the respective set of rate transformation values. In this way, a plurality of average relative transformation values is computed. In some embodiments, a measure of central tendency of the plurality of average relative transformation values is compared to an optional lookup table that matches the measure of central tendency of the plurality of average relative transformation values to a blood amount, thereby determining the amount of blood in the blood culture in the vessel.

In some embodiments, the amount of blood in the blood culture in the vessel is outputted to a user interface device, a monitor, a computer-readable storage medium, a computer-readable memory, or a local or remote computer system. In some embodiments, the amount of blood in the blood culture in the vessel is displayed. In some embodiments, the first time point is one or more hours after the initial time point and the second time point is four or more hours after the initial time point. In some embodiments, the first time point is between 1.5 hours and 3 hours after the initial time point and the second time point is between 4.5 hours and 5.5 hours after the initial time point.

In some embodiments, the measure of central tendency of a rate transformation value in a first set of rate transformation values in the plurality of sets of rate transformation values comprises a geometric mean, an arithmetic mean, a median, or a mode of each of the rate transformation values in the first set of rate transformation values. In some embodiments, the measure of central tendency of the plurality of average relative transformation values comprises a geometric mean, an arithmetic mean, a median, or a mode of the plurality of average relative transformation values.

In some embodiments, the measurements in the plurality of measurements of the biological state of the blood culture are each taken of the blood culture at a periodic time interval between the first time point and the second time point. For instance, in some embodiments, the periodic time interval is between one minute and twenty minutes, between five minutes and fifteen minutes, between thirty seconds and ten minutes, every 10 minutes, between 8 minutes and 12 minutes, etc.

In some embodiments, each average relative transformation value in the plurality of average relative transformation values that is below a first threshold or above a second threshold is removed from the plurality of average relative transformation values prior to computing the measure of central tendency of the plurality of average relative transformation values. In such embodiments, each average relative transformation value removed from the plurality of average relative transformation values does not affect the measure of central tendency of the plurality of average relative transformation values that is compared to the optional lookup table.

In some embodiments, the initial biological state of the blood culture is determined by a fluorescence output of a sensor that is in contact with the blood sample. For example, in some embodiments, the amount of fluorescence output of the sensor is affected by $CO_2$ concentration, $O_2$ concentration, or pH.

In some embodiments, between 10 and 50,000 measurements, between 100 and 10,000 measurements, between 150 and 5,000 measurements, between 100 and 1000 measurement, between 50 and 500 measurements, more than 10 measurements, or more than 100 measurements of the biological state of the blood culture in the vessel are made (e.g., made between a first time point and a second time point). In some embodiments, each respective predetermined fixed interval of time points comprises or consists of each of the rate transformation values for time points in a time window between the first time point and the second time point. In some embodiments, this time window is a period of time that is between twenty minutes and five hours, a period of time that is between twenty minutes and two hours, a period of time that is between thirty minutes and ninety minutes, a period of time that is between twenty minutes and an hour, or a period of time that is greater than thirty minutes.

In some embodiments, each set of rate transformation values in the plurality of rate transformation values comprises or consists of between four and twenty contiguous rate transformation values, between five and fifteen contiguous rate transformation values, between 2 and 1000 contiguous rate transformation values, or more than five rate transformation values. In some embodiments there are between five and five hundred, between twenty and one hundred, or between ten and ten thousand average relative transformation values in the plurality of average relative transformation values. In some embodiments, the amount of blood in the blood culture is between 1 ml and 150 ml, between 2 ml and 100 ml, between 0.5 ml and 80 ml, between 0.5 ml and 10,000 ml, or between 0.25 ml and 100,000 ml. In some embodiments, the blood culture is between 1 and 99 percent of the volume of the culture, between 5 and 80 percent of the volume of the culture, between 10 and 75 percent of the volume of the culture, less than 80 percent of the volume of the culture, or greater than 10 percent of the volume of the culture. In some embodiments, the blood culture is between 1 and 99 percent of the total weight of the culture, between 5 and 80 percent of the total weight of the culture, between 10 and 75 percent of the total weight of the culture, less than 80 percent of the total weight of the culture, or greater than 10 percent of the total weight of the culture.

In some embodiments, the vessel contains a sensor composition in fluid communication with the blood culture, where the sensor composition comprises a luminescent compound that exhibits a change in luminescent property, when irradiated with light containing wavelengths that cause said luminescent compound to luminesce, upon exposure to oxygen. Further, the presence of the sensor composition is non-destructive to the blood culture. In such embodiments the measurement of the initial biological state comprises irradiating the sensor composition with light containing wavelengths that cause said luminescent compound to luminesce and observing the luminescent light intensity from the luminescent compound while irradiating the sensor composition with the light. In some embodiments, the luminescent compound is contained within a matrix that is relatively impermeable to water and non-gaseous solutes, but which has a high permeability to oxygen. In some embodiments the matrix comprises rubber or plastic.

In another aspect, the present invention provides a blood amount determination apparatus that comprises a processor and a memory, coupled to the processor, for determining an amount of blood in a blood culture in a vessel. The memory can comprise an optional lookup table that comprises matches between (i) a first set of values for a measure of central tendency of a plurality of average relative transformation values and (ii) a set of blood amounts, where for each value for a measure of central tendency of a plurality of average relative transformation values in the first set of values, there is a corresponding blood amount in the set of blood amounts. In some embodiments the memory can comprise a blood amount determination module that comprises electronically encoded instructions that cause a processor (e.g., a microprocessor) to direct the automated measurement of an initial biological state of the blood culture in the vessel at an initial time point as well as electronically encoded instructions that cause a processor to direct the making of a plurality of measurements of a biological state of the blood culture in the vessel. Each measurement in the plurality of measurements is at a different time point between a first time point and a second time point. The blood amount determination module can further comprise instructions for calculating, for each respective measurement in the plurality of measurements, a normalization relative value between the respective measurement and the initial biological state of the blood culture thereby forming a plurality of normalization relative values.

The blood amount determination module can further comprise electronically encoded instructions for causing a processor to determine, for each respective predetermined fixed interval of time points between the first time point and the second time point, a first derivative of the normalization relative values in the respective predetermined fixed interval of time points, thereby forming a plurality of rate transformation values. The plurality of rate transformation values comprises a plurality of sets of rate transformation values, where each respective set of rate transformation values in the plurality of sets of rate transformation values is for a different set of contiguous time points between the first time point and the second time point. The blood amount determination module can further comprise electronically encoded instructions for causing a processor to compute, for each respective set of rate transformation values in the plurality of sets of rate transformation values, an average relative transformation value as a measure of central tendency of each of the rate transformation values in the respective set of rate transformation values, thereby computing a plurality of average relative transformation values. The blood amount determination module can further comprise electronically encoded instructions for causing a processor to compare a measure of central tendency of the plurality of average relative transformation values to the optional lookup table that matches the measure of central tendency of the plurality of average relative transformation values to a blood amount, thereby determining the amount of blood in blood culture in the vessel.

In another aspect, the present invention provides a computer-readable medium storing a computer program product for determining an amount of blood in a blood culture in a vessel, executable by a computer. The computer program product can comprise a lookup table that has matches between (i) a first set of values for a measure of central tendency of a plurality of average relative transformation values and (ii) a set of blood amounts, where, for each value for a measure of central tendency of a plurality of average relative transformation values in the first set of values, there is a corresponding blood amount in the set of blood amounts. The computer program product can further comprise the blood amount determination module described above in conjunction with the blood amount determination apparatus.

In another aspect, the present invention provides a blood amount determination apparatus that comprises a processor and a memory, coupled to the processor, for carrying out any of the methods disclosed herein. In still another aspect, the present invention provides a computer-readable medium storing a computer program product for determining an amount of blood in a blood culture in a vessel, executable by a computer. The computer program product comprises instructions for carrying out any of the methods disclosed herein.

In another aspect, the present invention provides a method of determining an amount of blood in a blood culture in a vessel. In the method, a plurality of measurements are obtained. Each measurement in the plurality of measurements taken at a different time point between a first time point and a second time point. Then for each respective predetermined fixed interval of time points between the first time point and the second time point, a first derivative of the measurements of the biological state in the respective predetermined fixed interval of time points is determined, thereby forming a plurality of rate transformation values. The plurality of rate transformation values comprises a plurality of sets of rate transformation values, where each respective set of rate transformation values in the plurality of sets of rate transformation values is for a different set of contiguous time points between the first time point and the second time point. For each respective set of rate transformation values in the plurality of sets of rate transformation values, an average relative transformation value is computed as a measure of central tendency of each of the rate transformation values in the respective set of rate transformation values, thereby computing a plurality of average relative transformation values. The amount of blood in the blood culture in the vessel based is then determined based on the measure of central tendency of the plurality of average relative transformation values. In some embodiments, this determining step comprises comparing the measure of central tendency of the plurality of average relative transformation values to a lookup table that matches the measure of central tendency of the plurality of average relative transformation values to a blood amount, thereby determining the amount of blood in the blood culture in the vessel. In other embodiments, this determining step may be accomplished by an equation that provides blood volume as a function of the measure of central tendency of the plurality of average relative transformation values.

4 BRIEF DESCRIPTION OF THE DRAWINGS

Like reference numerals refer to corresponding parts throughout the several views of the drawings.

5 DETAILED DESCRIPTION OF THE INVENTION

Figure 1:
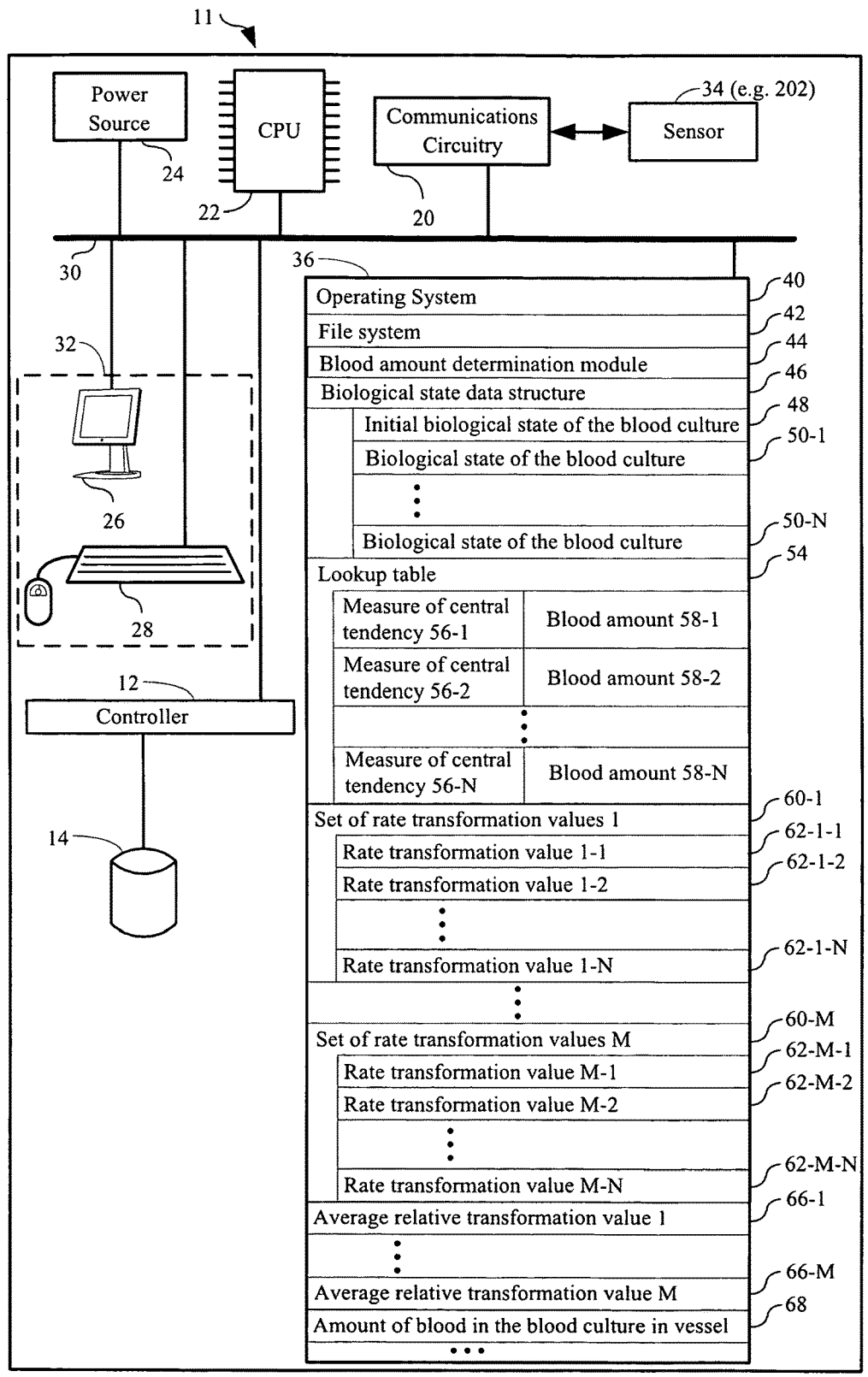
FIG. 1 illustrates a blood amount determination apparatus comprising a processor and a memory, coupled to the processor, for determining an amount of blood in a blood culture in a vessel in accordance with an embodiment of the present invention.

Systems, methods and apparatus for determining an amount of blood in a blood culture are provided where an initial biological state and then periodic measurements of the biological state of the culture are taken. For each respective measurement, a normalization relative value between the respective measurement and the initial measurement is made thereby forming normalization relative values. For each interval of time points represented by the normalization relative values, a first derivative of the normalization relative values in the interval is made thereby forming a plurality of rate transformation values. For each set of rate transformation values in the plurality of rate transformation values, an average relative transformation value is computed, thereby forming a plurality of average relative transformation values. A lookup table that matches a measure of central tendency of the average relative transformation values to a blood amount can be used to determine the amount of blood in the blood culture.

5.1 Definitions

The term "biological state" as used herein refers to a measure of the metabolic activity of a blood culture as determined by, for example, $CO_2$ concentration, $O_2$ concentration, pH, a rate of change in $CO_2$ concentration, a rate of change in $O_2$ concentration, or a rate of change in pH in the blood culture.

The term "blood" as used herein means either whole blood or any one, two, three, four, five, six, or seven cell types from the group of cells types consisting of red blood cells, platelets, neutrophils, eosinophils, basophils, lymphocytes, and monocytes. Blood can be from any species including, but not limited to, humans, any laboratory animal (e.g., rat, mouse, dog, chimp), or any mammal.

The term "blood culture" as used herein refers to any amount of blood that has been mixed with blood culture media. Examples of culture media include, but are not limited to, supplemented soybean casein broth, soybean casein digest, hemin, menadione, sodium bicarbonate, sodium polyaneltholesulfonate, sucrose, pyridoxal HCKI, yeast extract, and L-cysteine. One or more reagents that may be used as blood culture media are found, for example, in Stanier et al., 1986, *The Microbial World*, 5$^{th}$ edition, Prentice-Hall, Englewood Cliffs, N.J., pages 10-20, 33-37, and 190-195, which is hereby incorporated by reference herein in its entirety for such purpose. In some instances, a blood culture is obtained when a subject has symptoms of a blood infection or bacteremia. Blood is drawn from a subject and put directly into a vessel containing a nutritional broth. In some embodiments, ten milliliters of blood is needed for each vessel.

As used herein, the term "instance" refers to the execution of a step in an algorithm. Some steps in an algorithm may be run several times, with each repeat of the step being referred to as an instance of the step.

As used herein, the term "microorganism" refers to organisms with a diameter of 1 mm or less other than viruses.

As used herein, the term "portion" refers to at least one percent, at least two percent, at least ten percent, at least twenty percent, at least thirty percent, at least fifty percent, as least seventy-five percent, at least ninety percent, or at least 99 percent of a set. Thus, in a nonlimiting example, at least a portion of a plurality of objects means at least one percent, at least two percent, at least ten percent, at least twenty percent, at least thirty percent, at least fifty percent, as least seventy-five percent, at least ninety percent, or at least 99 percent of the objects in the plurality.

As used herein, a "subject" is an animal, preferably a mammal, more preferably a non-human primate, and most preferably a human. The terms "subject", "individual" and "patient" are used interchangeably herein.

As used herein, the term "vessel" refers to any container that can hold a culture such as a blood culture. For instance, in one embodiment a vessel is a container having a side wall, a bottom wall, an open top end for receiving a culture to be contained within the container, where the container is formed from a material such as glass, clear plastic (e.g., a cyclic olefin copolymer) having a transparency sufficient to visually observe turbidity in the sample, and where the is preferably resistant to heating at a temperature of at least 250° C. In some embodiments, the container has a wall thickness sufficient to withstand an internal pressure of at least 25 psi and a closure coupled to the open end of the container, where the culture is substantially free of contamination after storage in the vessel for an extended period of time under ambient conditions. Exemplary containers are described in U.S. Pat. No. 6,432,697, which is hereby incorporated herein by reference. In some embodiments, the extended period of time under ambient conditions is at least about one year at about 40° C. In some embodiments, the vessel further comprises a fluorescent sensor compound fixed to an inner surface of the container that, when exposed to oxygen, exhibits a reduction in fluorescent intensity upon exposure to a fluorescing light. In some embodiments, the container is substantially transparent to said fluorescing light. In some embodiments, the fluorescent sensor compound comprises at least one compound selected from the group consisting of tris-4,7-diphenyl-1,10-phenanthroline ruthenium (II) salts, tris-2,2'-bipyridyl ruthenium (II) salts, 9,10-diphenyl anthracene, and mixtures thereof. In some embodiments, a vessel is a Blood Culture BACTEC®LYTIC/10 Anaerobic/F culture vial, a BBL® SEPTI-CHEK® vial, a BBL® SEPTI-CHEK® blood culture bottle, a Becton Dickinson BACTEC® vial, a Plus Aerobic/F* and Plus Anaerobic/F* culture vial, a Becton Dickinson BACTEC®Standard/10 Aerobic/F culture vial, a Becton Dickinson BACTEC® Myco/F Lytic culture vial, a Becton Dickinson BACTEC® PEDS PLUS®/F culture vial, or a Becton Dickinson BACTEC® Standard Anaerobic/F culture vial (Becton Dickinson, Franklin Lakes, N.J.).

5.2 Exemplary Apparatus

FIG. 1 details an exemplary blood amount determination apparatus 11 comprising a processor and a memory, coupled to the processor, for determining an amount of blood in a blood culture in a vessel. The processor and memory illustrated in FIG. 1 can be part of, for example, an automated or semiautomated radiometric or nonradiometric blood culture system. The apparatus 11 can comprise:
  a central processing unit 22;
  optionally, a main non-volatile storage unit 14, for example a hard disk drive, for storing software and data, the storage unit 14 controlled by storage controller 12;
  a system memory 36, preferably high speed random-access memory (RAM), for storing system control programs, data, and application programs, comprising programs and data (optionally loaded from non-volatile storage unit 14); system memory 36 may also include read-only memory (ROM);
  a user interface 32, comprising one or more input devices (e.g., keyboard 28, a mouse) and a display 26 or other output device;
  a sensor 34 for taking a measurement of a biological state of a culture in a vessel;

a network interface card 20 (communications circuitry) for connecting to the sensor 34;

an internal bus 30 for interconnecting the aforementioned elements of the system; and a power source 24 to power the aforementioned elements.

Operation of central processing unit 22 is controlled primarily by operating system 40. Operating system 40 can be stored in system memory 36. In a typical implementation, system memory 36 also includes:

a file system 42 for controlling access to the various files and data structures used by the present invention;

a blood amount determination module 44 for determining the amount (e.g., volume) of blood in a blood culture;

a biological state data structure 46 for storing an initial biological state 48 of the blood culture and a plurality of measurements of the biological state of the blood culture, where each measurement 50 in the plurality of measurements is taken at a different time point between a first (initial) time point and a second (final) time point;

an optional lookup table 54 that comprises matches between (i) a first set of values for a measure of central tendency of a plurality of average relative transformation values and (ii) a set of blood amounts, wherein, for each value for a measure of central tendency of a plurality of average relative transformation values in the first set of values, there is a corresponding blood amount in the set of blood amounts;

sets of rate transformation values 60, where each set of rate transformation values comprises a plurality of rate transformation values 62, where each rate transformation value 62 is a first derivative of the normalization relative values associated with a predetermined fixed interval of time points;

an average relative transformation value 66 for each set 60 of rate transformation values 60; and a data structure 68 for storing a value indicative of the amount of blood in a culture in a vessel.

As illustrated in FIG. 1, apparatus 11 can comprise data such as biological state data structure 46, optional lookup table 54, sets of rate transformation values 60, average relative transformation values 66, and an amount of blood 68 in the blood culture in a vessel. In some embodiments, memory 36 or data store 14 also stores a measure of central tendency of the average relative transformation values 66. The data described above can be in any form of data storage including, but not limited to, a flat file, a relational database (SQL), or an on-line analytical processing (OLAP) database (MDX and/or variants thereof). In some embodiments, such data structures are stored in a database that comprises a star schema that is not stored as a cube but has dimension tables that define hierarchy. Still further, in some embodiments, such data structures are stored in a database that has hierarchy that is not explicitly broken out in the underlying database or database schema (e.g., dimension tables that are not hierarchically arranged). In some embodiments, such data structures are stored in apparatus 11. In other embodiments, all or a portion of these data structures are hosted on (stored on) one or more computers that are addressable by apparatus 11 across an Internet/network that is not depicted in FIG. 1. In some embodiments, all or a portion of one or more of the program modules depicted in apparatus 11 of FIG. 1, such as blood amount determination module 44 are, in fact, resident on a device (e.g., computer) other than apparatus 11 that is addressable by apparatus 11 across an Internet/network that is not depicted in FIG. 1.

Apparatus 11 determines the metabolic activity of a blood culture by, for example, $CO_2$ concentration, $O_2$ concentration, pH, a rate of change in $CO_2$ concentration, a rate of change in $O_2$ concentration, or a rate of change in pH in the blood culture. From this metabolic activity determination, apparatus 11 can determine the amount of blood in a blood culture. In some embodiments, apparatus 11 accommodates a number of blood culture vessels and serves as an incubator, agitator, and detection system. These components of apparatus 11 are not depicted in FIG. 1 because the nature of such components will vary widely depending on the exact configuration of apparatus 11. For instance, the number of culture vessels accommodated by apparatus can range from one vessel to more than 1000 vessels. There can be a sensor associated with each vessel in order to measure the biological state of the blood culture contained within the vessel. The sensor can be on any location of the vessel and there are a wide range of possible sensors that can be used.

Figure 2:
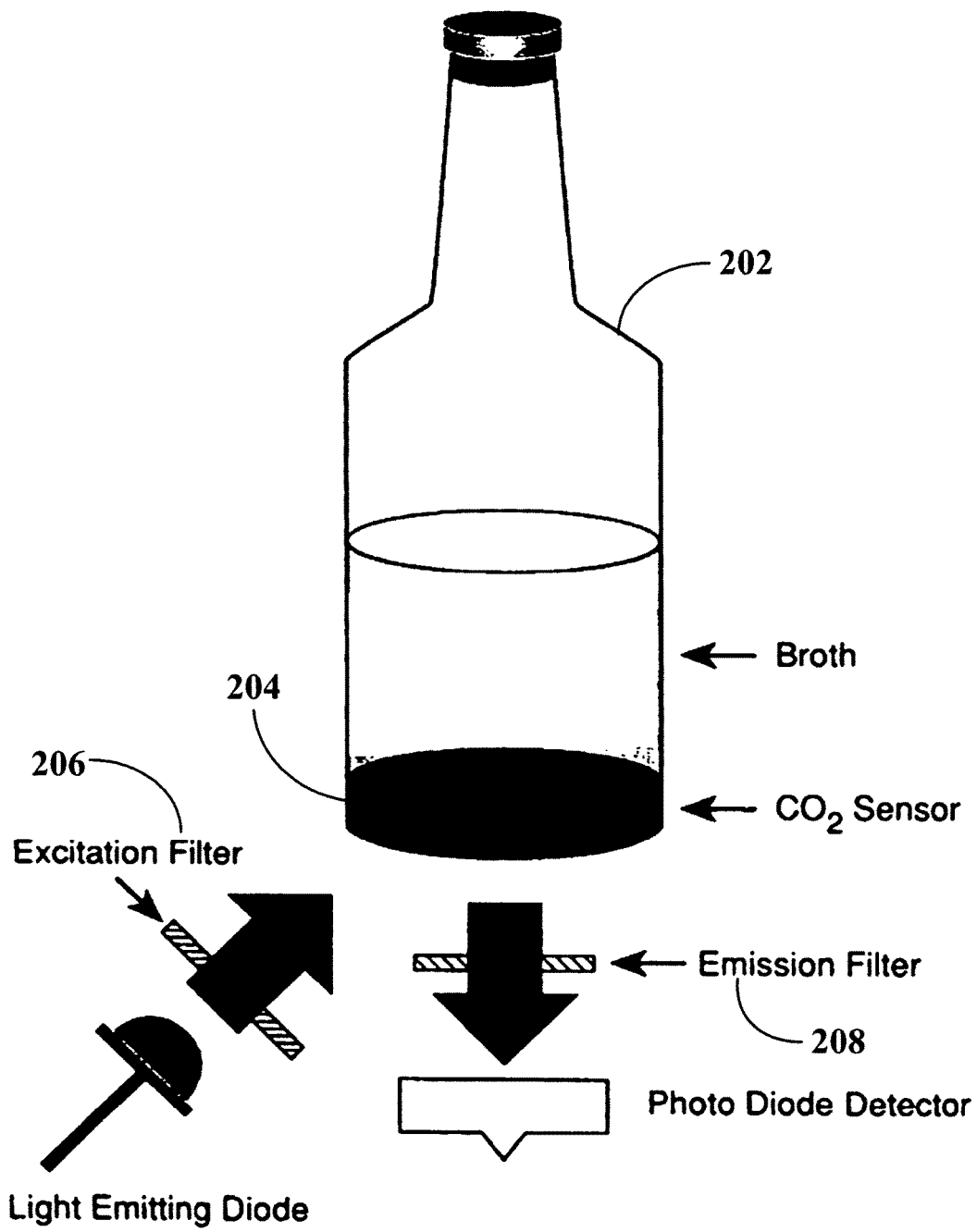
FIG. 2 illustrates a schematic drawing of a blood culture vessel and $CO_2$ detector system in accordance with an embodiment of the present invention.

FIG. 2 illustrates one exemplary sensor that is capable of measuring the biological state of the blood culture. In FIG. 2, a $CO_2$ sensor 204 is bonded to the base of blood culture vessel 202 and overlaid with an amount of blood culture which comprises a mixture of blood and culture media. $CO_2$ sensor 204 is impermeable to ions, medium components, and blood but is freely permeable to $CO_2$. Carbon dioxide produced by the blood diffuses into sensor 204 and dissolves in the water present in the sensor matrix, generating hydrogen ions. Increases in hydrogen ion concentration (decreases in pH) increase the fluorescence output of sensor 204, thereby changing the signal transmitted from excitation filter 206 to emission filter 208. Apparatus 11 takes repeated measurements of the signal penetrating emission filter 208 over time and uses this data to determine the amount of blood in a blood culture using the algorithms disclosed herein.

In some embodiments, apparatus 11 is an incubator, shaker, and fluorescence detector that will hold between 1 and 1000 culture vessels (e.g., 96, 240 or 384 culture vessels). In some embodiments, the vessels are arranged in racks (e.g., circular or linear racks), each of which has a number of vessel stations. For example, in one specific embodiment, apparatus 11 will hold 240 vessels arranged in six racks, where each rack has 40 vessel stations. In some embodiments, each vessel station in apparatus 11 contains a light-emitting diode and a photo diode detector with appropriate excitation and emission filters (e.g., as illustrated in FIG. 2). In some embodiments, the vessels are rocked and heated at 35±1° C.

5.3 Exemplary Methods

Now that an exemplary apparatus in accordance with the present invention has been described, exemplary methods in accordance with the present invention will be detailed. In some embodiments, such methods can be implemented by blood amount determination module 44 of FIG. 1. Without wishing to be bound by any particular method or theory, the principle of blood amount determination is based on measuring the initial relative metabolic rate of the blood in the sample upon entry into the system. Blood is a suspension of living eukaryotic cells and when placed in a culture medium they continue to metabolize for as much as 48 hours after entry into the system. The rate of initial metabolism and in some cases the rate of decline in initial metabolism can provide information on the amount of blood cells (therefore the blood amount) present in the blood culture. Referring to step 302 of FIG. 3, an initial biological state of the blood culture is taken. For example, referring to FIG. 2, in some embodiments, an initial read of detector 204 is made to determine the $CO_2$ concentration in the sensor. In alternative embodiments, an initial $O_2$ concentration, pH, or other indicia of the biological state of the culture is read (measured) in step 302. In some embodiments, the initial biological state of the blood culture is determined by a fluorescence output of a sensor (e.g., sensor 204) that is in contact with the blood culture. In some embodiments, the amount of fluorescence output of the sensor is affected by $CO_2$ concentration in the manner described above in conjunction with FIG. 2. In some embodiments, the amount of fluorescence output of the sensor is affected by $O_2$ concentration, pH, or some other indicia of metabolic state known in the art. In general, any observable parameter of a culture (e.g., $O_2$ concentration, $CO_2$, concentration, etc.) that is indicative of the metabolic rate of the culture can be measured and stored as the initial state. In some embodiments, this physical observable is the accumulation of molecular products (an example being lipopolysaccharide with Gram negative bacteria), non-molecular physical/chemical changes to the environment related to growth (pressure changes), and/or the production of carbon dioxide or other metabolites that accumulate or the consumption of substrate such as oxygen) or the accumulation of cell material.

In some embodiments, an initial biological state of the blood culture is taken in step 302 using colorimetric means, fluorometric means, nephelometric means, or infrared means. Examples of colorimetric means include, but are not limited to, the use of the colorimetric redox indicators such as resazurine/methylene blue or tetrazolium chloride, or the of p-iodonitrotetrazolium violet compound as disclosed in U.S. Pat. No. 6,617,127 which is hereby incorporated by reference herein in its entirety. Another example of colorimetric means includes the colormetric assay used in Oberoi et al. 2004, "Comparison of rapid colorimetric method with conventional method in the isolation of *Mycobacterium tuberculosis*," Indian J Med Microbiol 22:44-46, which is hereby incorporated by reference herein in its entirety. In Oberoi et al., a MB/Bact240 system (Organon Teknika) is loaded with culture vessels. The working principle of this system is based on mycobacterial growth detection by a colorimetric sensor. If the organisms are present, $CO_2$ is produced as the organism metabolizes the substrate glycerol. The color of the gas permeable sensor at the bottom of each culture vessel results in increase of reflectance in the unit, which is monitored by the system using infrared rays. Examples of colorimetric means further include any monitoring of the change in a sensor composition color due to a change in gas composition, such as $CO_2$ concentration, in a vessel resulting from microorganism metabolism.

Examples of fluorometric and colorimetric means are disclosed in U.S. Pat. No. 6,096,272, which is hereby incorporated by reference herein in its entirety, which discloses an instrument system in which a rotating carousel is provided for incubation and indexing, and in which there are multiple light sources each emitting different wavelength light for colorimetric and fluorometric detection. As used herein nephelometric means refers to the measurement of culture turbidity using a nephelometer. A nephelometer is an instrument for measuring suspended particulates in a liquid or gas colloid. It does so by employing a light beam (source beam) and a light detector set to one side (usually 90°) of the source beam. Particle density is then a function of the light reflected into the detector from the particles. To some extent, how much light reflects for a given density of particles is dependent upon properties of the particles such as their shape, color, and reflectivity. Therefore, establishing a working correlation between turbidity and suspended solids (a more useful, but typically more difficult quantification of particulates) must be established independently for each situation.

As used herein, an infrared means for measuring a biological state of a blood culture is any infrared microorganism detection system or method known in the art including, but not limited to, those disclosed U.S. Pat. No. 4,889,992, as well as PCT publication number WO/2006071800, each of which is hereby incorporated by reference herein in its entirety.

In some embodiments, the vessel 202 holding the blood culture comprises a sensor composition 204 in fluid communication with the blood culture. The sensor composition 204 comprises a luminescent compound that exhibits a change in luminescent property, when irradiated with light containing wavelengths that cause the luminescent compound to luminesce, upon exposure to oxygen. The presence of the sensor composition 204 is non-destructive to the blood culture. In such embodiments, the measuring step 302 (and each instance of the measuring step 308) comprises irradiating the sensor composition 202 with light containing wavelengths that cause the luminescent compound to luminesce and observing the luminescent light intensity from the luminescent compound while irradiating the sensor composition with the light. In some embodiments, the luminescent compound is contained within a matrix that is relatively impermeable to water and non-gaseous solutes, but which has a high permeability to oxygen. In some embodiments, the matrix comprises rubber or plastic. More details of sensors in accordance with this embodiment of the present invention are disclosed in U.S. Pat. No. 6,900,030 which is hereby incorporated by reference herein in its entirety.

In step 304, the measured initial biological state of the blood culture upon initialization from step 302 is standardized and stored as the initial biological state of the blood culture 48 (e.g. to one hundred percent or some other predetermined value). This initial biological state, stored as data element 48 in FIG. 1, serves as a reference value against subsequent measurements of the biological state of the blood culture. In some embodiments, step 304 is not performed and the absolute measurements of step 302 are used in the algorithms disclosed herein.

Figure 3A:
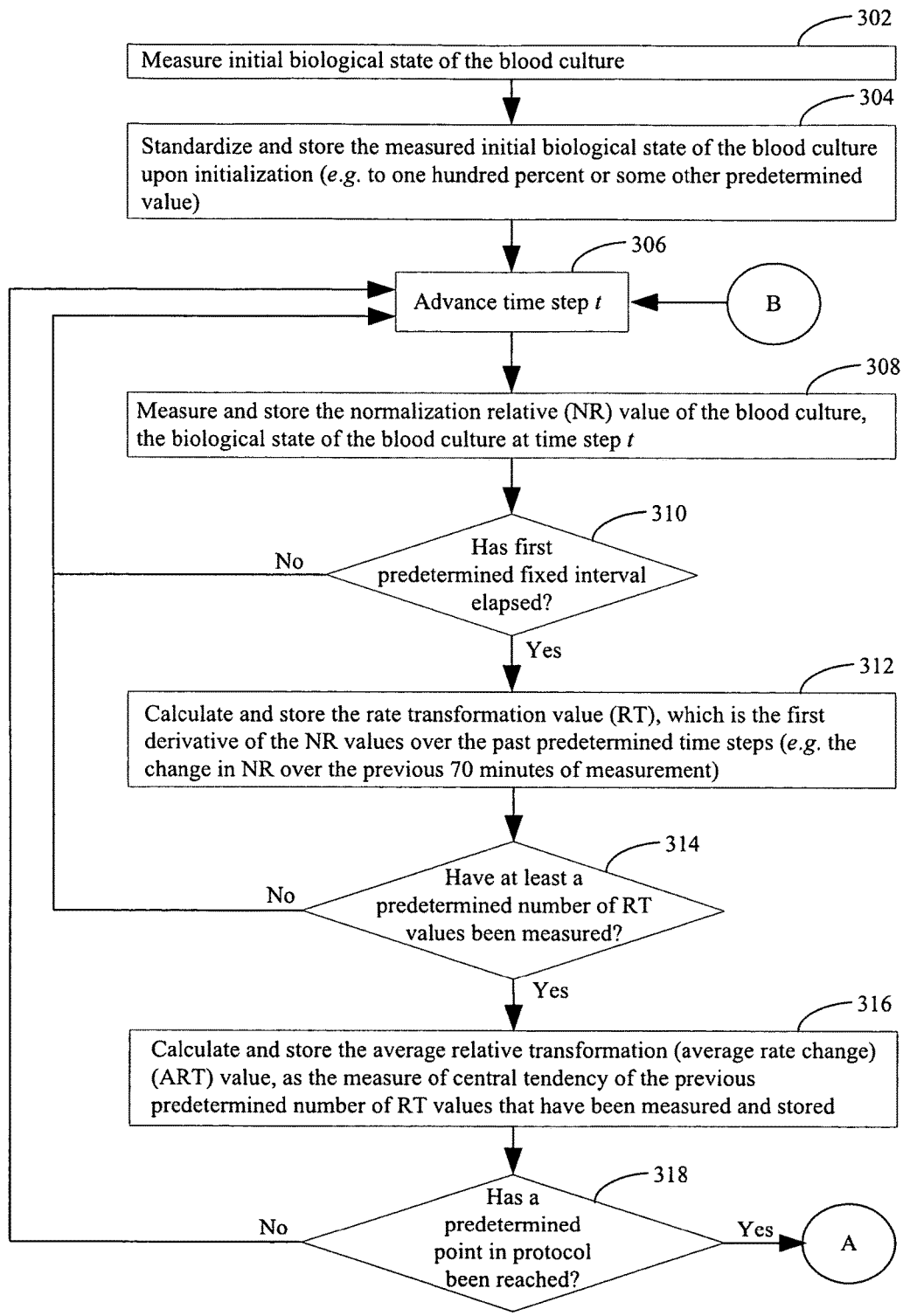
FIGS. 3A and 3B illustrate a method of determining an amount of blood in a blood culture in a vessel in accordance with an embodiment of the present invention.
Figure 3B:
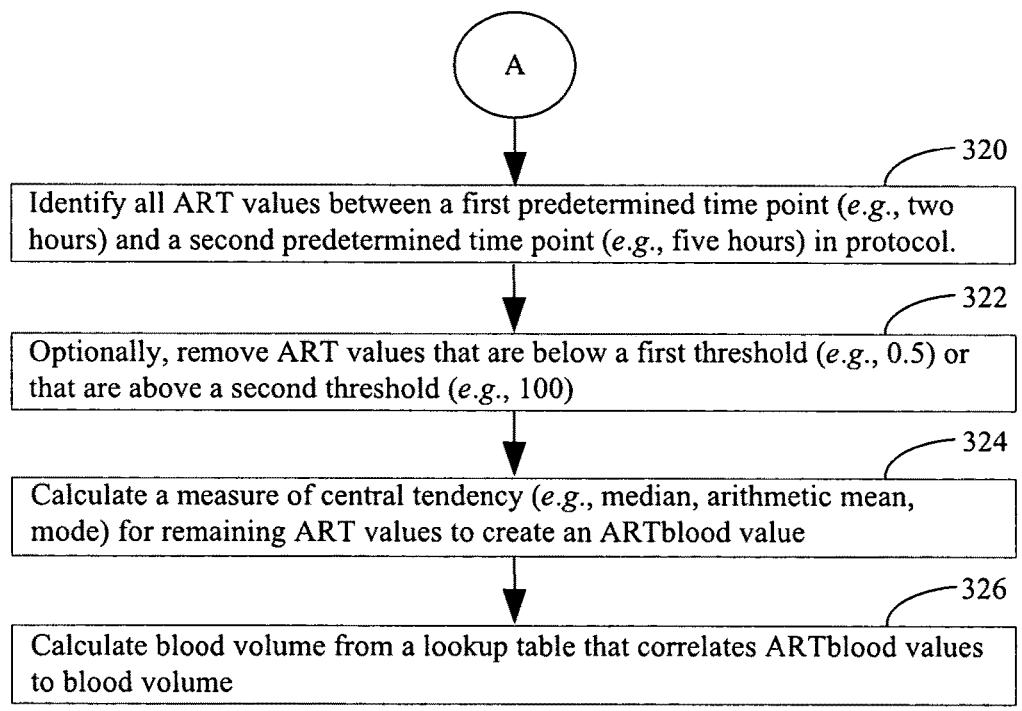

Apparatus 11 incubates the blood culture for a predetermined period of time after the initial biological state measurement is taken. Then, after the predetermined period of time has elapsed, apparatus 11 makes another measurement of the biological state of the blood culture. This process is illustrated by steps 306 and 308 in FIG. 3. In FIG. 3A, the process is shown as advancing to time step t in step 306. The biological state during the time period in step 306 in which apparatus waits for time to advance by time step t is not used in subsequent processing steps to ascertain the amount of blood in the blood culture. In step 308, once time has advanced by time step t, a measurement of the biological state of the blood culture in the vessel is again taken in the same manner that the initial measurement of the biological state was taken (e.g., using the device depicted in FIG. 2). In some embodiments, the predetermined period of time (the duration of time step t) is ten minutes. In some embodiments, the predetermined period of time (the duration of time step t) is a period of time that is less than 5 minutes, a period of time that is less than 10 minutes, a period of time that is less than 15 minutes, a period of time that is less than 20 minutes, a period of time in the range between 1 minute and 30 minutes, or a period of time that is greater than 5 minutes. In some embodiments, measurement of the biological state of the blood culture is taken in step 308 using colorimetric means, fluorometric means, nephelometric means, or infrared means. The measurement of the biological state of the blood culture in the vessel taken in step 308 is converted to a normalization relative value by standardizing the measurement of step 308 against the initial measurement of step 302 in embodiments where the initial measurement of step 302 is used for normalization. In one embodiment, the measurement of the biological state of the blood culture in the vessel taken in step 308 is converted to a normalization relative value by taking the ratio of the measurement of step 308 against the initial measurement of step 302. In some embodiments, this computed normalization relative value is stored as a data element 50 in FIG. 1. In some embodiments, the measurement of the biological state measured in step 308 is stored as a data element 50 in FIG. 1 and the normalization relative value corresponding to the measurement of the biological state measured in step 308 is computed as needed in subsequent processing steps.

In step 310 a determination is made as to whether a first predetermined fixed time interval has elapsed. For example, in some embodiments the predetermined fixed time interval is seventy minutes. In this example, if the time step t of step 306 is 10 minutes, then it would require time step t to have advanced seven times before condition 310—Yes is achieved. In some embodiments, the predetermined fixed interval of time is a duration of time that is between five minutes and five hours, a duration of time that is between thirty minutes and ten hours, a duration of time that is less than 24 hours, or a duration of time that is more than 24 hours. When the first predetermined fixed interval of time has elapsed (310—Yes), process control passes on to step 312 where additional steps of the algorithm are performed. When the first predetermined fixed interval of time has not elapsed (310—No), process control passes back to step 306 where the algorithm waits for time to advance by the amount of time t prior to once again taking a measurement of the biological state of the blood culture in a new instance of step 308.

The net result of steps 306 through 310 is that a plurality of measurements of a biological state of the blood culture in the vessel are taken and that each measurement in the plurality of measurements is at a different time point between a first (initial) time point and a terminating (final) time point. Further, in typical embodiments where time step t is the same amount in each instance of step 306, the measurements in the plurality of measurements are each taken of the blood culture at a periodic interval. In some embodiments, the periodic interval is an amount of time between one minute and twenty minutes, an amount of time between five minutes and fifteen minutes, an amount of time between thirty seconds and five hours, or an amount of time that is greater than one minute.

When a predetermined fixed interval has elapsed (310—Yes), a first derivative of the normalization relative values in the respective predetermined fixed interval (or absolute values from step 302 in the respective predetermined fixed interval in embodiments in which normalization is not performed) is computed in step 312, thereby forming a rate transformation value 62. In other words, the change in the normalization relative values during the predetermined fixed interval is determined in step 312. Note that rate transformation values are the first derivative of normalization relative values in embodiments where measurement data is normalized and rate transformation values are the first derivative of absolute measurements from step 302 in embodiments where measurement data is not normalized. In some embodiments, the predetermined fixed interval of time over which the first derivative is computed is all measurements in an immediately preceding period of time that is between twenty minutes and two hours. For example, in some embodiments the predetermined fixed interval of time of step 310 is seventy minutes and, in step 312, the rate of change across all of the normalization relative values of measurements in this seventy minute time interval (the past 70 minutes) is determined in step 312 and stored as the rate transformation value 62. In some embodiments, the predetermined fixed interval of time over which the first derivative is computed (time window) is all measurements in an immediately preceding period of time that is between five minutes and twenty hours, between thirty minutes and ten hours, between twenty minutes and two hours, between twenty minutes and ten hours, or between thirty minutes and ninety minutes.

In step 314 a determination is made as to whether a predetermined number of rate transformation values have been measured since the last time condition 314—Yes was reached. If so (314—Yes), process control passes on to step 316. If not (314—No), process control returns back to step 306 where process control waits until time step t has elapsed before continuing to step 308 where the normalization relative value of the blood culture is once again calculated. Each condition (314—Yes) marks the completion of a set 60 of rate transformation values 62. For example, in some embodiments, condition 314—Yes is achieved when seven new rate transformation values 62 have been measured. In this example, a set 60 of rate transformation values comprises or consists of the seven rate transformation values. In some embodiments, each set 60 of rate transformation values 62 comprises or consists of between four and twenty contiguous rate transformation values 62. Contiguous rate transformation values 62 are rate transformation values in the same set 60. Such rate transformation values 62 are, for example, calculated and stored in successive instances of step 312. In some embodiments, each set 60 of rate transformation values 62 in the plurality of rate transformation values comprises or consists of between five and fifteen contiguous rate transformation values 62, between one and one hundred contiguous rate transformation values 62, more than five rate transformation values 62, or less than ten rate transformation values 62.

When condition 314—Yes is achieved, step 316 is run. In step 316, an average relative transformation (average rate of change) value 66 is computed from the newly formed set 60 of rate transformation values 62. Thus, for each set 60 of rate transformation values 62, there is an average relative transformation value 66. In some embodiments, an average relative transformation (average rate of change) value 66 is computed from the newly formed set 60 of rate transformation values 62 by taking a measure of central tendency of the rate transformation values 62 in the newly formed set 60 of rate transformation values 62. In some embodiments, this measure of central tendency is a geometric mean, an arithmetic mean, a median, or a mode of all or a portion of the rate transformation values 62 in the newly formed set 60 of rate transformation values 62.

In step 318, a determination is made as to whether a predetermined point in the protocol has been reached. This predetermined point is a final time point, also known as an end point or second time point. In some embodiments, the second time point is reached (318—Yes) one or more hours, two or more hours, ten or more hours, between three hours and one hundred hours, or less than twenty hours after the initial measurement in step 302 was taken. In some embodiments, the second time point is reached (318—Yes) when between 10 and 50,000, between 100 and 10,000, or 150 and 5,000, more than 10, more than fifty, or more than 100 measurements of the biological state of the blood culture in the vessel have been made in instances of step 308. If the predetermined point in the protocol has not been reached (318—No), then process control returns to step 306 where the process control waits for time step t to advance before initiating another instance of step 308 in which the biological state of the blood culture is again measured and used to calculate a normalization relative value. If the predetermined point in the protocol has been reached (318—Yes), process control passes to step 320.

In step 320, all average relative transformation (average rate of change) values 66 between a first predetermined time point and a second predetermined time point in protocol are identified. In some embodiments all average relative transformation values 66 calculated in successive instances of step 316 are considered to be between the first predetermined time point and the second predetermined time point. In such embodiments, step 320 is not required. In some embodiments, the first time point is one or more hours after the initial time point in step 302 when the initial biological state measurement was made and the second time point is four or more hours after the initial time point. In some embodiments, the first time point is between 1.5 hours and 3 hours after the initial time point and the second time point is between 4.5 hours and 5.5 hours after the initial time point. In some embodiments, the first time point is between 0.5 hours and 10 hours after the initial time point and the second time point is after the first time point and between 5 hours and 30 hours after the initial time point.

In optional step 322, average relative transformation values 66 that are below a first threshold or above a second threshold are removed. In some embodiments, the first threshold is a value between 0.01 and 5 (e.g., 0.5). In some embodiments, the second threshold is a value between 50 and 500 (e.g., 100). Each average relative transformation value removed from the plurality of average relative transformation values in step 322 does not affect the measure of central tendency of the plurality of average relative transformation values 66 that is computed in step 324.

In step 324, a measure of central tendency of all average relative transformation values 66, aside from any removed in optional step 322) is calculated. In some embodiments the measure of central tendency is a geometric mean, an arithmetic mean, a median, or a mode of the plurality of average relative transformation values 66. In some embodiments there are between five and five hundred, between twenty and one hundred, more than 100, or less than 10,000 average relative transformation values 66 in the plurality of average relative transformation values.

In some embodiments of step 326, the measure of central tendency of the plurality of average relative transformation values 66 computed in step 324 is used to find a match in an optional lookup table 54. As illustrated in FIG. 1, lookup table 54 comprises a plurality of measures of central tendency 56 and a plurality of blood amounts 58. For each measure of central tendency 56 in the plurality of measures of central tendency 56 there is a corresponding blood amount 58 in the plurality of blood amounts. In step 326, the measure of central tendency 56 that is the closest match to the measure of central tendency computed in step 324 is determined. Then, the blood amount 58 that corresponds to this identified measure of central tendency 56 is deemed to be the amount of blood 68 that is in blood culture in the vessel. Lookup table 54 is constructed at a time prior to step 326 using calibrated amounts of blood in blood culture. In some embodiments the amount of blood 68 in the blood culture is expressed in units of volume. For instance, in some embodiments the amount of blood 68 in the blood culture is between 1 ml and 40 ml, between 2 ml and 10 ml, or between 1 ml and 1000 liters. In some embodiments, the amount of blood 68 in the blood culture is expressed in terms of weight, mass, concentration, or some other metric. In some embodiments, rather than using an optional lookup table, one or more trained classifier or other forms of waited equations are used to determine blood volume.

In some embodiments, the method further comprises outputting the amount of blood 68 in the blood culture in the vessel to a user interface device (e.g., 32), a monitor (e.g., 26), a computer-readable storage medium (e.g., 14 or 36), a computer-readable memory (e.g., 14 or 36), or a local or remote computer system. In some embodiments the amount of blood in the blood culture in the vessel is displayed. As used herein, the term local computer system means a computer system that is directly connected to apparatus 11. As used herein, the term remote computer system means a computer system that is connected to apparatus 11 by a network such as the Internet.

5.4 Exemplary Computer Program Products and Computers

The present invention can be implemented as a computer program product that comprises a computer program mechanism embedded in a computer-readable storage medium. Further, any of the methods of the present invention can be implemented in one or more computers. Further still, any of the methods of the present invention can be implemented in one or more computer program products. Some embodiments of the present invention provide a computer program product that encodes any or all of the methods disclosed herein. Such methods can be stored on a CD-ROM, DVD, magnetic disk storage product, or any other computer-readable data or program storage product. Such methods can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. Such methods encoded in the computer program product can also be distributed electronically, via the Internet or otherwise, by transmission of a computer data signal.

Some embodiments of the present invention provide a computer program product that contains any or all of the program modules and data structures shown in FIG. 1. These program modules can be stored on a CD-ROM, DVD, magnetic disk storage product, or any other computer-readable data or program storage product. The program modules can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. The software modules in the computer program product can also be distributed electronically, via the Internet or otherwise, by transmission of a computer data signal.

5.5 Kits

Some embodiments of the invention may also comprise a kit to perform any of the methods described herein. In a non-limiting example, vessels, culture for blood, and additional agents, and software for performing any combination of the methods disclosed herein may be comprised in a kit. The kits will thus comprise one or more of these reagents in suitable container means.

The components of the kits, other than the software, vessels, and the radiometric or nonradiometric system, may be packaged either in aqueous media or in lyophilized form. The suitable container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present invention also will typically include a means for containing the reagent containers in close confinement for commercial sale. Such containers may include injection or blow-molded plastic containers into which the desired vials are retained.

6 EXAMPLE

A method for the determination of a volume of a biological sample in a culture vessel was developed. The method set forth herein exemplifies use of this method in the BACTEC® Blood culture system (Becton Dickenson Diagnostic Instrument Systems, Sparks, Md.) for determining a volume of blood in a blood culture. The BACTEC® Blood culture system uses fluorescent sensors to monitor the changes in metabolic activity within the reagent through a stream of compensated fluorescence signal data that was collected at ten minute intervals from a sensor located inside the culture reagent. The data used in this example was collected from the BACTEC® instruments used either in internal seeded culture studies or collected during a clinical evaluation of the system. The data was sorted and collected into a database that includes the identification of the vessel (by sequence and accession numbers), a record of the dates of inoculation, and the amount of blood in the sample. Data transformations of the present invention were applied subsequently for analysis.

The data transformations begin with an initial normalization of the vessel signal to a specific output (its initial state upon entering the system), termed the initial biological state 48 of blood culture, and all subsequent data (biological states at subsequent time intervals) was represented as a percentage of that initial signal (which was standardized to 100 percent in these analyses). As data was collected in the system, the data points were accumulated as a percentage of this initial signal. Each of these data points, expressed as a percentage of the initial signal, was a normalization relative value (NR) value.

The next value that was computed was the first derivative of the NR value as they change with time. This value is the rate transformation (RT) value 62. The base RT value used in these analyses uses a periodicity limit of seventy minutes. Any given RT value 62 represents the rate of percentage change of fluorescence signal over the seventy minutes prior to its calculation.

The next value that was computed was the average rate transformation (ART) value 62. The ART value 66 was calculated as the average of the previous 7 RT values 50 that have been calculated and acts as a smoothing function of the RT values 50.

Figure 4:
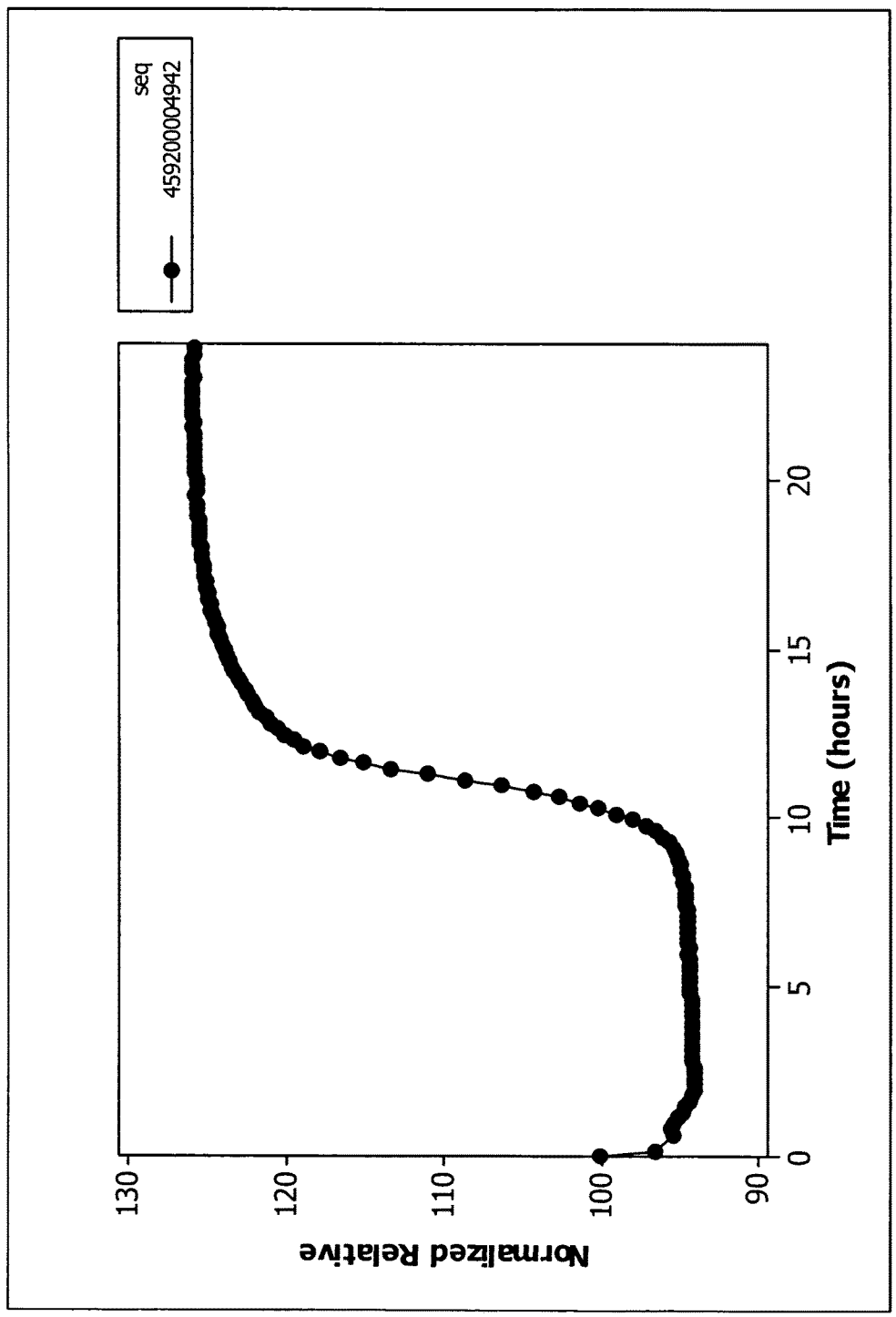
FIG. 4 shows a plot of normalization relative values measured from a blood culture in a vessel in accordance with an embodiment of the present invention.
Figure 5:
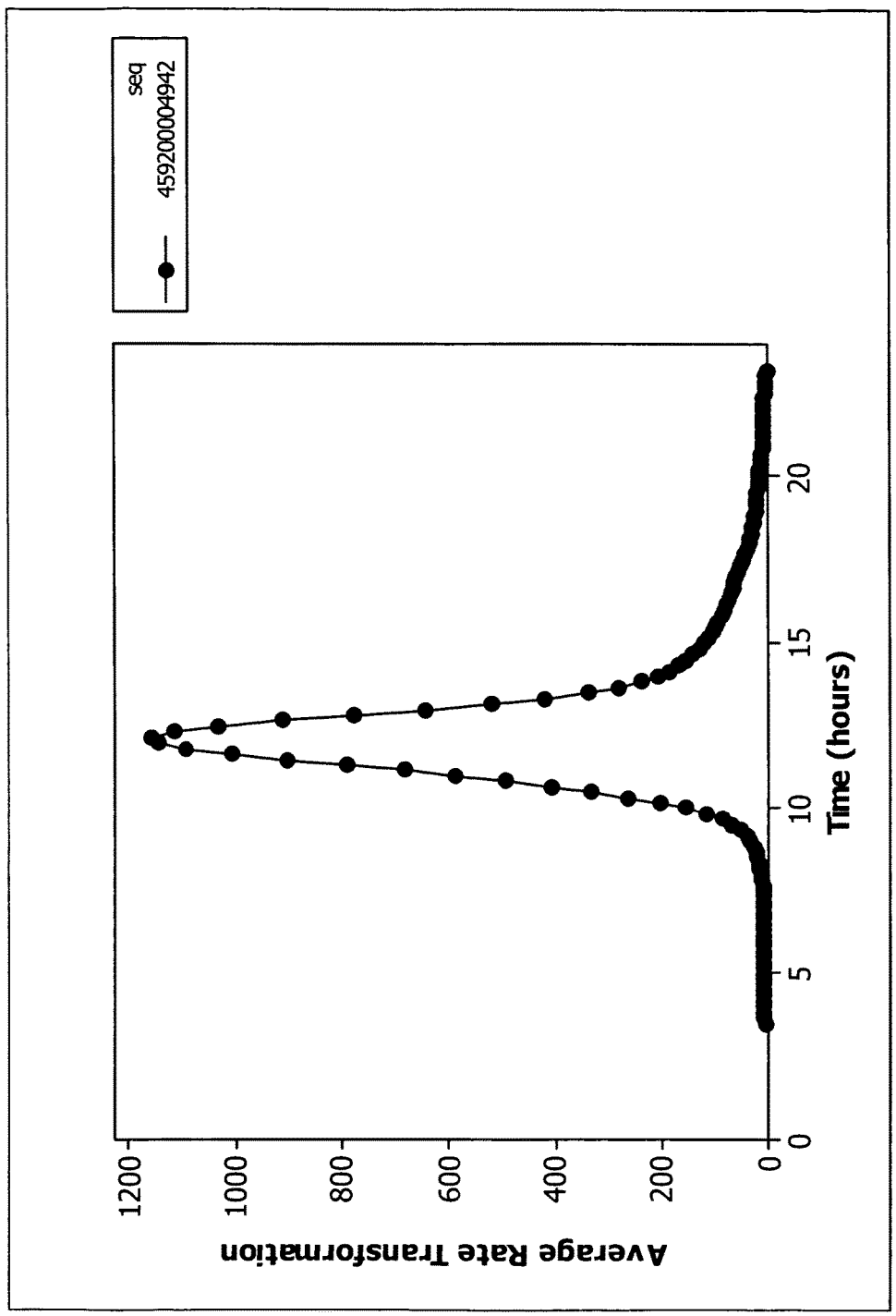
FIG. 5 is a plot of the average relative transformation values over time based on the average rate of change in rate transformation values of FIG. 4 over time in accordance with an embodiment of the present invention.
Figure 6:
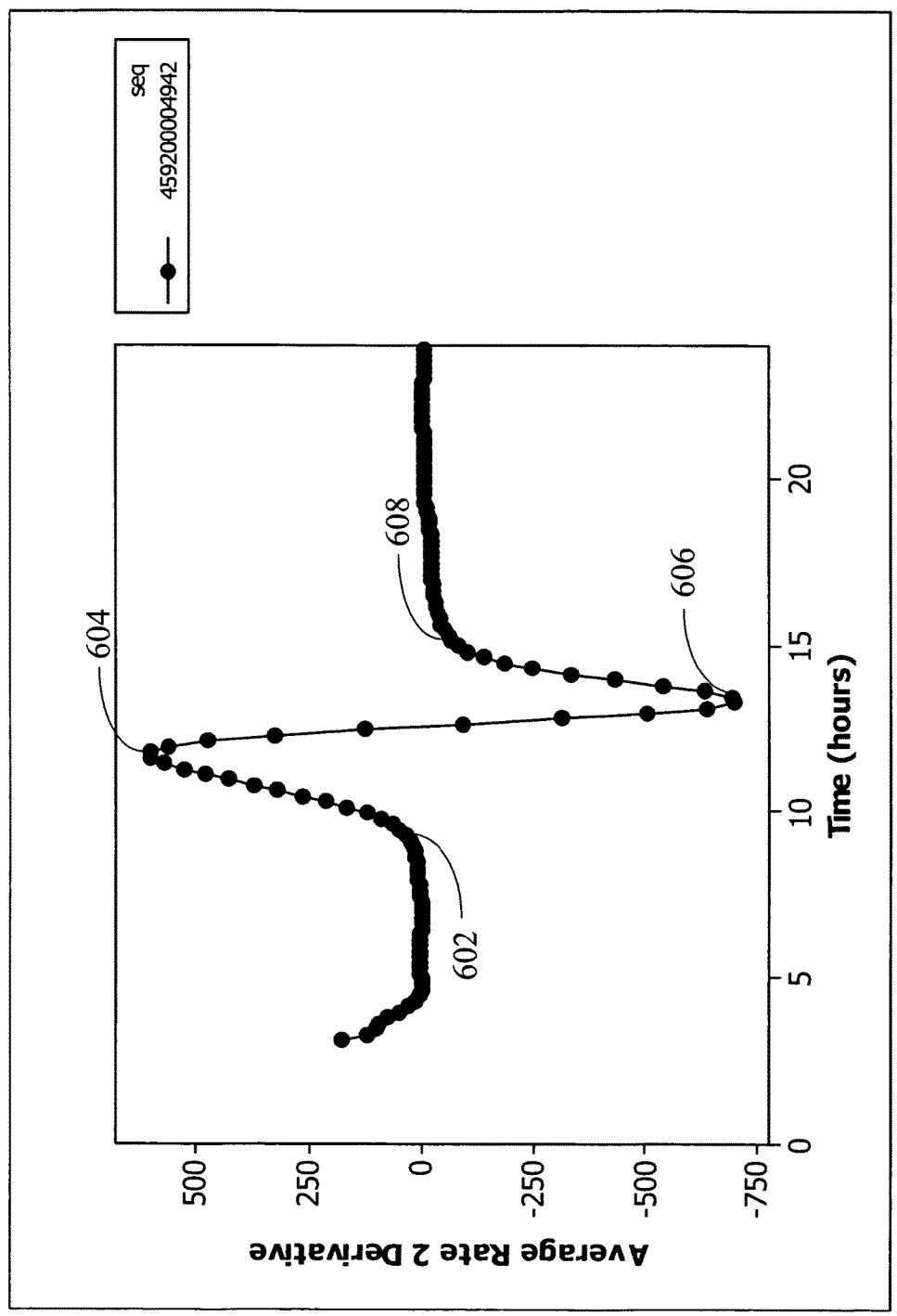
FIG. 6 is the second derivative plot of normalization relative values of FIG. 4 and shows the changes in metabolism rate with time in accordance with an embodiment of the present invention.

Examples of the parameters that were computed to determine blood volume are presented in FIGS. 4, 5 and 6. An *Escherichia coli* culture was analyzed using these quantitative metrics (the normalized relative values 50, the rate transformation values 62, and the average relative transformation values 66. The culture contained three milliliters of human blood from a subject and was inoculated with a suspension of *E. coli* (55 CFU) and entered into a BACTEC® 9000 instrument. The sequence 4942 is a unique identifier of a culture that is reported in FIGS. 4, 6, and 6 that can be used to link the data for this culture to a research and development BACTEC® database. FIG. 4 shows a plot of normalization relative values over time. The vessel was entered into the instrument and temperature affects related to equilibration of the vessel were observed for approximately the first hour. The signal stabilized and a background was observed to increase from 94 percent to 95 percent of the initial signal for the first hour (this rate was due to blood activity). In the normalization relative plot (FIG. 4), growth was visible beginning at eight hours and proceeded until 15 hours with a final value NR value near 126. The plot of average relative transformation values 66 over time based on the average rate of change in rate transformation values 62 of FIG. 4 over time is provided in FIG. 5. Each average relative transformation (ART) value 66 is a measure of the average rate of change and the maximum ART for this culture was 1158 achieved at 12.8 hours into the culture. This represents this culture's averaged maximum achieved rate of sensor change over a one hour period. FIG. 6 is the second derivative plot of normalization relative values 50 and shows the changes in rate with time. This is a graphical interpretation showing the following critical points: the point of initial acceleration 602 (movement from the null), the point of maximum acceleration 604 (the maxima), where acceleration reaches its maximum (crossing the null point), the maximum point of deceleration (the minima) 606, and the terminus of the growth curve 608 (where the rate change returns to null).

Figure 7:
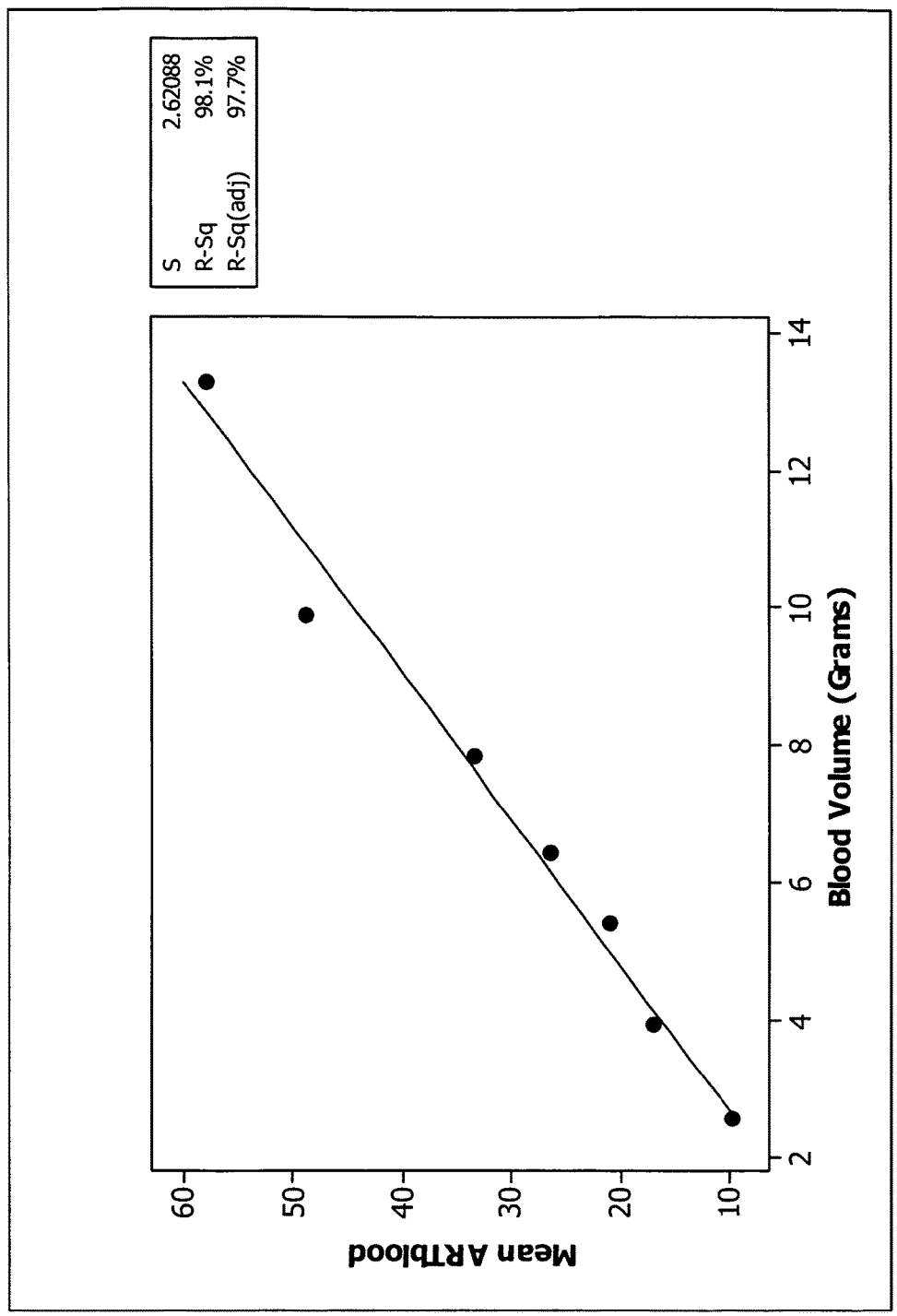
FIG. 7 illustrates the plot of mean ARTblood values (defined herein as a measure of central tendency of select average relative transformation values) against corresponding blood volume values with a regression line demonstrating 98.1% correlation between the mean ARTblood value and blood volume in accordance with an embodiment of the present invention.
Figure 8:
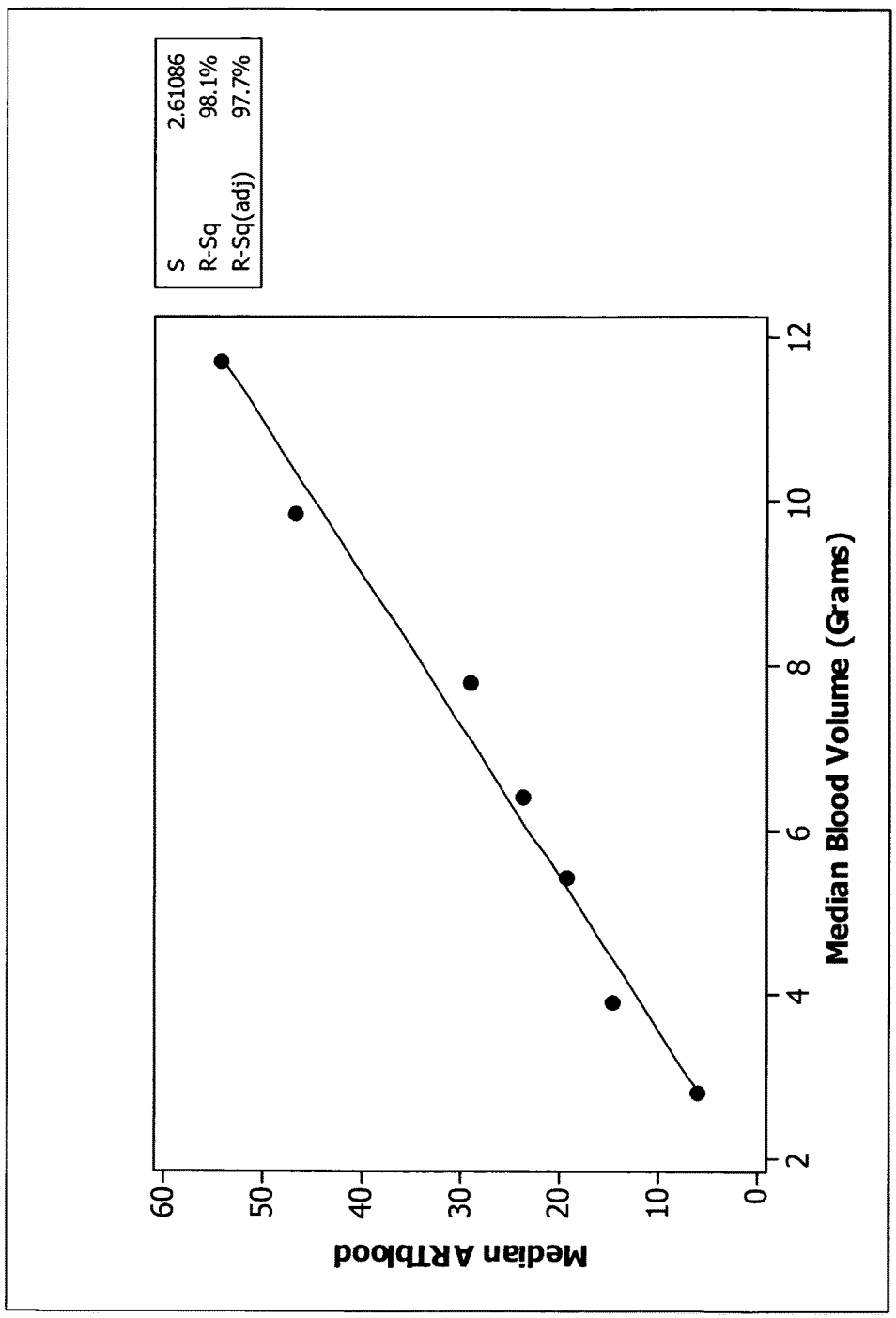
FIG. 8 illustrates the plot of median ARTblood values against corresponding blood volume values with a regression line demonstrating 98.1% correlation between the median ARTblood value and blood volume in accordance with an embodiment of the present invention.

The application of the above-identified transformations in the blood culture system 11 allowed an early look at what was occurring metabolically in the vessel in the first two to five hours after the vessel was entered into system 11. Advantageously, as illustrated in FIGS. 7 and 8, the measure of central tendency of the average relative transformation values could be correlated to the volume of blood in the test sample. The data presented was generated from an extensive data set derived from an external evaluation of a modified aerobic plus medium. The calculations used to generate FIGS. 7 and 8 comprises considering only average relative transformation values 66 for the period greater than or equal to 2.5 hours in protocol and less than or equal to 5 hours in protocol. Average relative transformation values 66 in this time frame less than 0.5 and greater than 100 were discarded. An ARTblood value (defined herein as a measure of central tendency of select average relative transformation values) was taken as a measure of central tendency of the remaining average relative transformation values 66. The data was averaged in sets that corresponded to measured blood volumes (bins were used to segregate the sets into 2 ml blood volume ranges and in some cases these bins were split for the analysis). The mean (FIG. 7) and median (FIG. 8) ARTblood values were then plotted against the corresponding blood volume values with regression lines that demonstrated 98.1% correlation between the ARTblood values (mean and median) and the blood volumes. Advantageously, this blood volume measuring technique can be applied to the clinical laboratory to provide the necessary feedback to the laboratory staff to help them perform quality control and to optimize the use of the blood culture system 11.

7 REFERENCES CITED

All references cited herein are incorporated herein by reference in their entirety and for all purposes to the same extent as if each individual publication or patent or patent application was specifically and individually indicated to be incorporated by reference in its entirety herein for all purposes.

8 MODIFICATIONS

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed:

1. An apparatus comprising:
   (1) a processor;
   (2) a sensor that measures a $CO_2$ concentration, an $O_2$ concentration, a pH, a rate of change in $CO_2$ concentration, a rate of change in $O_2$ concentration, or a rate of change in pH as a measure of a biological state of a blood culture disposed in a vessel, wherein the sensor measures the biological state of the blood culture at a plurality of time points between a first time point and a second time point, and wherein the blood culture comprises a blood sample and a blood culture media;
   (3) a memory comprising:
      (a) a first threshold of a minimum acceptable blood amount;
      (b) a second threshold of a maximum acceptable blood amount;
      (c) a lookup table comprising matches between a plurality of measures of central tendency and a plurality of blood amounts; and
      (d) a blood amount determination module comprising:
         (i) electronically encoded instructions that calculate a plurality of rate transformation values, wherein each rate transformation value is derived from a different subset of the measurements of the biological state of the blood culture made by the sensor within a predetermined time interval between the first time point and the second time point;
         (ii) electronically encoded instructions that calculate a plurality of average rate transformation values, wherein each average rate transformation value is derived from a different subset of the rate transformation values;
         (iii) electronically encoded instructions that calculate a measure of central tendency from one or more of the average rate transformation values; and
         (iv) electronically encoded instructions that determine the amount of blood in the blood culture in the vessel by comparing the measure of central tendency to one or more of the measures of central tendency in the lookup table; and (4) a user interface that displays a warning if the determined amount of blood in the blood culture in the vessel is below the first threshold or above the second threshold.

2. The apparatus of claim 1, wherein the user interface is also configured to display the determined amount of blood in the blood culture in the vessel.

3. The apparatus of claim 1, wherein each rate transformation value is a first derivative of a different subset of the measurements of the biological state of the blood culture made by the sensor within a predetermined time interval.

4. The apparatus of claim 1, wherein the blood amount determination module further comprises electronically encoded instructions that convert the measurements of the biological state of the blood culture into normalization relative values.

5. The apparatus of claim 4, wherein each rate transformation value is a first derivative of a different subset of the normalization relative values within a predetermined time interval.

6. The apparatus of claim 1, wherein all of the predetermined time intervals have the same duration.

7. The apparatus of claim 6, wherein the rate transformation values are calculated and stored in successive instances.

8. The apparatus of claim 7, wherein the average rate transformation values are calculated and stored in successive instances.

9. The apparatus of claim 1, wherein the measure of central tendency is a geometric mean, an arithmetic mean, a median, or a mode of one or more of the average rate transformation values.

10. The apparatus of claim 1, wherein the blood amount determination module further comprises electronically encoded instructions that remove average rate transformation values below a third threshold or above a fourth threshold.

11. The apparatus of claim 1, wherein the sensor comprises at least one of colorimetric means, fluorometric means, nephelometric means, or infrared means.

12. A method comprising:
   (1) obtaining a vessel with a blood culture disposed therein, wherein the blood culture comprises a blood sample and a blood culture media;
   (2) measuring, with a sensor, a $CO_2$ concentration, an $O_2$ concentration, a pH, a rate of change in $CO_2$ concentration, a rate of change in $O_2$ concentration, or a rate of change in pH as a measure of a biological state of the blood culture at a plurality of time points between a first time point and a second time point;
   (3) determining with a processor, an amount of blood in the blood culture in the vessel, in part, by:
      (a) calculating a plurality of rate transformation values, wherein each rate transformation value is derived from a different subset of the measurements of the biological state of the blood culture within a predetermined time interval between the first time point and the second time point;
      (b) calculating a plurality of average rate transformation values, wherein each average rate transformation value is derived from a different subset of the rate transformation values;
      (c) calculating a measure of central tendency from one or more of the average rate transformation values; and
      (d) determining the amount of blood in the blood culture in the vessel by comparing the measure of central tendency to one or more measures of central tendency in a lookup table comprising matches between a plurality of measures of central tendency and a plurality of blood amounts;

(4) comparing, with the processor, the determined amount of blood in the blood culture in the vessel to a first predetermined threshold of a minimum acceptable blood amount and a second predetermined threshold of a maximum acceptable blood amount; and (5) providing, with a user interface, a warning to a user if the determined amount of blood in the blood culture in the vessel is below the first threshold or above the second threshold.

13. The method of claim 12 further comprising:
displaying the determined amount of blood in the blood culture in the vessel to the user.

14. The method of claim 12, wherein each rate transformation value is a first derivative of a different subset of the measurements of the biological state of the blood culture within a predetermined time interval.

15. The method of claim 12, wherein determining the amount of blood in the blood culture in the vessel further comprises converting the measurements of the biological state of the blood culture into normalization relative values.

16. The method of claim 15, wherein each rate transformation value is a first derivative of a different subset of the normalization relative values within a predetermined time interval.

17. The method of claim 12, wherein all of the predetermined time intervals have the same duration.

18. The method of claim 17, wherein the rate transformation values are calculated and stored in successive instances.

19. The method of claim 18, wherein the average rate transformation values are calculated and stored in successive instances.

20. The method of claim 12, wherein the measure of central tendency is a geometric mean, an arithmetic mean, a median, or a mode of one or more of the average rate transformation values.

21. The method of claim 12, wherein determining the amount of blood in the blood culture in the vessel further comprises removing average rate transformation values below a third threshold or above a fourth threshold.

22. The method of claim 12, wherein the sensor comprises at least one of colorimetric means, fluorometric means, nephelometric means, or infrared means.

* * * * *